United States Patent
Cembrowski et al.

(10) Patent No.: US 10,338,085 B2
(45) Date of Patent: Jul. 2, 2019

(54) DEVICES AND METHODS TO DETERMINE WHETHER TO CALIBRATE A LABORATORY ANALYZER

(71) Applicants: George S. Cembrowski, Edmonton (CA); Mark A. Cervinski, Lebanon, NH (US)

(72) Inventors: George S. Cembrowski, Edmonton (CA); Mark A. Cervinski, Lebanon, NH (US)

(73) Assignee: CCQCC CORP., Alberta (CA)

( * ) Notice: Subject to any disclaimer, the term of this patent is extended or adjusted under 35 U.S.C. 154(b) by 994 days.

(21) Appl. No.: 14/743,712

(22) Filed: Jun. 18, 2015

(65) Prior Publication Data
US 2016/0370394 A1    Dec. 22, 2016

(51) Int. Cl.
*G01N 35/00* (2006.01)
*G04F 10/00* (2006.01)

(52) U.S. Cl.
CPC . *G01N 35/00712* (2013.01); *G01N 35/00693* (2013.01); *G01N 35/00594* (2013.01); *G04F 10/00* (2013.01)

(58) Field of Classification Search
CPC ....... G01N 35/00712; G01N 35/00693; G01N 35/00623; G01N 33/492; G01N 35/00603; G01N 35/00613; G01F 19/36
See application file for complete search history.

(56) References Cited

U.S. PATENT DOCUMENTS

2011/0022343 A1*   1/2011   Cembrowski .... G01N 35/00613
                                                                    702/85

OTHER PUBLICATIONS

Cembrowski, Thoughts on quality-control systems: a laboratorian's perspective, 1997, Clinical Chemistry, 43:5, pp. 886-892.*
Cembrowski, G.S., et al., "Assessment of "Average of Normals" Quality Control Procedures and Guidelines for Implementation", American Journal of Clinical Pathology, 81, (Apr. 1984), 492-499.
Hoffman, R.G., et al., "The "Average of Normals" Method of Quality Control", The American Journal of Clinical Pathology, 43, (1965), 134-141.

(Continued)

*Primary Examiner* — Sujoy K Kundu
*Assistant Examiner* — L. Anderson
(74) *Attorney, Agent, or Firm* — Schwegman Lundberg & Woessner, P.A.

(57) ABSTRACT

Generally discussed herein are systems, apparatuses, and methods that relate to detecting an error in a laboratory analyzer. A device may include an average of deltas (AoD) module to receive pairs of consecutive measurement values of an analyte of one or more patients, each pair of consecutive measurement values including a first measurement of an analyte obtained from a patient of the one or more patient at a first time and a second measurement of an analyte obtained from the patient at a second time after the first time, determine a time delta between each pair of consecutive measurement values, determine whether the time delta is within a specified time window, determine a measurement value deltas between each pair of consecutive measurement values that includes a time delta with the specified time window, and determine an AoD using the determined measurement value deltas.

17 Claims, 8 Drawing Sheets

(56) References Cited

OTHER PUBLICATIONS

Jones, G.R.D., "Average of Delta—A New Concept in Quality Control", Presentation, SydPath, St. Vincent's Hospital, Sydney, Australia, 2004. Retrieved from the Internet: <URL: www.sydpath.stvincents.com.au/other/Presentations/AveOfDelta04.ppt>, 13 p.

Jones, G.R.D., "Average of Normals", Presentation, Australasian Association of Clinical Biochemists, 2004. Retrieved from the Internet: <URL: http://www.aacb.asn.au/documents/item/1186>, 50 p.

Jones, Graham R. D., "Average of delta: a new quality control tool for clinical laboratories", *Annals of Clinical Biochemistry*, (May 6, 2015), 1-8.

\* cited by examiner

| PATIENT | DATE | TIME 1 | VALUE 1 | DATE | TIME 2 | VALUE 2 | DATE | TIME 3 | VALUE 3 | DATE | TIME 4 | VALUE 4 |
|---|---|---|---|---|---|---|---|---|---|---|---|---|
| A | 10-Dec | 819 | 4.3 | 11-Dec | 832 | 4.79 | 12-Dec | 815 | 4.15 | 13-Dec | 912 | 4.35 |
| B | 10-Dec | 821 | 3.68 | 11-Dec | 1204 | 3.54 | 12-Dec | 601 | 3.32 | 13-Dec | 820 | 3.47 |
| C | 10-Dec | 823 | 3.85 | 11-Dec | 834 | 3.94 | 12-Dec | 635 | 3.66 | 13-Dec | 825 | 4.06 |
| D | 10-Dec | 825 | 4.24 | 11-Dec | 335 | 4.28 | 12-Dec | 820 | 4.01 | 13-Dec | 835 | 4.23 |
| E | 10-Dec | 827 | 3.87 | 11-Dec | 1208 | 3.77 | 12-Dec | 640 | 3.99 | 13-Dec | 845 | 3.83 |
| F | 10-Dec | 829 | 3.99 | 12-Dec | 915 | 3.83 | 13-Dec | 815 | 4.23 | 14-Dec | 912 | 4.07 |
| G | 10-Dec | 831 | 3.84 | 10-Dec | 959 | 3.46 | 10-Dec | 1212 | 3.64 | 10-Dec | 1400 | 3.44 |

*FIG. 3*

| PATIENT | TIME DELTA 1 | VALUE DELTA 1 | TIME DELTA 2 | VALUE DELTA 2 | TIME DELTA 3 | VALUE DELTA 3 |
|---|---|---|---|---|---|---|
| A | 24h 13m | -0.49 | 23h 43m | 0.64 | 24h 57m | -0.2 |
| B | 27h 43m | 0.14 | 17h 57m | 0.22 | 24h 19m | -0.15 |
| C | 24h 11m | -0.09 | 21h 59m | 0.28 | 25h 50m | -0.4 |
| D | 19h 10m | -0.04 | 28h 45m | 0.27 | 24h 15m | -0.22 |
| E | 27h 41m | 0.1 | 18h 32m | -0.22 | 26h 05m | 0.16 |
| F | 48h 46m | 0.16 | 23h 00m | -0.4 | 24h 57m | 0.16 |
| G | 1h 28m | 0.38 | 2h 13m | -0.18 | 1h 48m | 0.2 |

| ANALYTE | INDUCED ERROR | ANDD | SD | MODE NDD | MEDIAN NDD |
|---|---|---|---|---|---|
| ALBUMIN | -0.4 mg/dL | 8.796438 | 3.47576 | 7 | 8 |
|  | +0.4 mg/dL | 24.64631 | 18.7309 | 9 | 19 |
| ALT | -7 U/L | 36.97382 | 24.47162 | 18 | 28 |
|  | +7 U/L | 33.06283 | 22.93552 | 15 | 25 |
| AMYLASE | -20 U/L | 12.4 | 6.618157 | 5 | 11 |
|  | +20 U/L | 6.2 | 3.34664 | 4 | 5 |
| BICARB | -4 mmol/L | 11.68595 | 7.938783 | 8 | 9 |
|  | +4 mmol/L | 14.59847 | 12.09785 | 8 | 10 |
| CALCIUM | -1 mg/dL | 6.47981 | 5.060369 | 5 | 5 |
|  | +1 mg/dL | 11.86223 | 10.78646 | 5 | 8 |
| CREATININE | -0.3 mg/dL | 43.05392 | 23.97218 | 33 | 33 |
|  | +0.3 mg/dL | 44.61115 | 25.72438 | 33 | 33 |
| GLUCOSE | -6 mg/dL | 161.451 | 114.9518 | 84 | 122 |
|  | +6 mg/dL | 180.5708 | 127.3456 | 76 | 139 |
| MAGNESIUM | -0.11 mmol/L | 16.47913 | 7.790218 | 14 | 14 |
|  | +0.11 mmol/L | 19.91808 | 11.4581 | 14 | 15 |
| POTASSIUM | -0.5 mmol/L | 50.12903 | 26.35253 | 38 | 39 |
|  | +0.5 mmol/L | 88.89578 | 59.29699 | 36 | 71 |
| SODIUM | -4 mmol/L | 19.74568 | 15.95917 | 12 | 12 |
|  | +4 mmol/L | 17.6963 | 13.08518 | 12 | 12 |

DEVICES AND METHODS TO DETERMINE WHETHER TO CALIBRATE A LABORATORY ANALYZER

TECHNICAL FIELD

Embodiments in this disclosure generally relate to devices and methods for detecting error in a clinical laboratory analyzer, such as to determine whether the analyzer needs maintenance, such as calibration.

BACKGROUND

It is estimated that as much as eight hundred fifty billion dollars is spent on needless medical procedures each year in the United States. One or more methods or devices discussed herein may help reduce the amount of money spent on wasteful medical procedures.

BRIEF DESCRIPTION OF THE DRAWINGS

In the drawings, which are not necessarily drawn to scale, like numerals may describe similar components in different views. The drawings illustrate generally, by way of example, but not by way of limitation, various embodiments discussed in the present document.

FIG. 3 illustrates, by way of example, a table of potassium measurement values for a variety of patients and over a variety of time ranges.

FIG. 4 illustrates, by way of example, a table of time deltas and value deltas corresponding to the time values and measurement values of the table 3 of FIG. 3.

DESCRIPTION OF EMBODIMENTS

Figure 1:
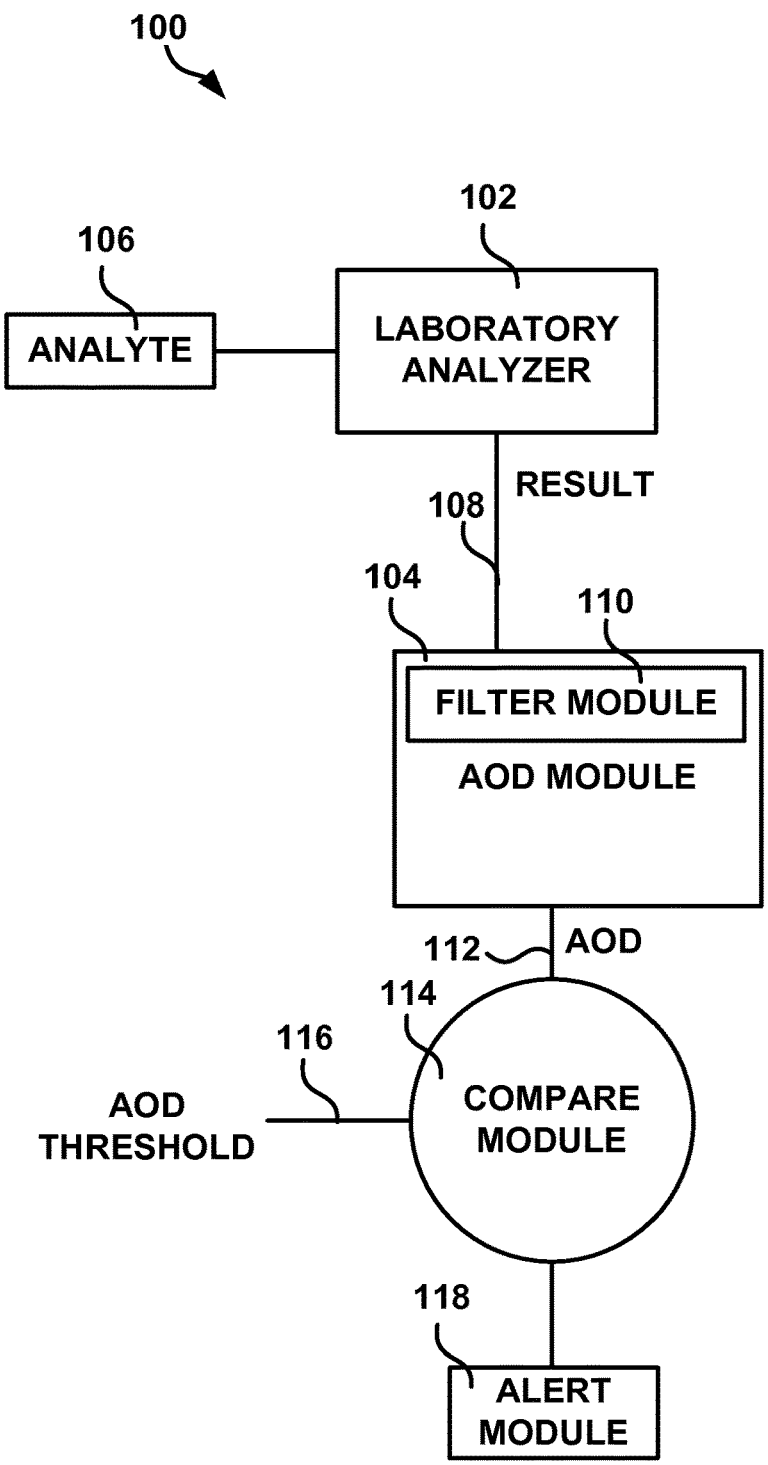
FIG. 1 illustrates, by way of example, a block diagram of an embodiment of a system to determine whether a laboratory analyzer requires just re-calibration or a more complete investigation.

Embodiments in this disclosure relate generally to detecting error in a laboratory analyzer. Methods, systems, or devices in accord with this disclosure may help in determining if a laboratory analyzer should be calibrated or otherwise requires an adjustment. Methods, systems, or devices in accord with this disclosure may help in determining the appropriateness of re-analyzing a specimen associated with an analyzer error signal.

Modern laboratory equipment (e.g., chemistry and hematology analyzers, or the like) should be precise and accurate. Laboratory analyzers may be calibrated with calibrating solutions where the calibration can be verified by an analysis of quality control specimens. If the laboratory analyzer returns the value that is expected for the control specimen within a specified tolerance, then the laboratory analyzer is considered calibrated. If not, then operation of the laboratory analyzer is investigated, possibly repaired, and may be re-calibrated so that the analyzer returns quality control results within the specified tolerance. On such systems, once the analysis of one or more quality control specimens confirms that an analytical run is accurate, the laboratorian generally assumes that the prevalence of analytically defective testing is very low. For this reason, quality control specimens may be analyzed infrequently. Quality control specimen analysis is often used to confirm the expected absence of analytical shifts and increased random error and not to detect error. With analytic errors that are episodic (e.g., periodic and/or transient), it is possible that quality control results may be within tolerance specifications, while preceding and/or subsequent analyses are defective but not detected. This problem of undetected error may be attributed to infrequent control analyses.

To detect these intermittent errors, quality control specimens might be analyzed more frequently. Such a solution requires scheduling more tests on laboratory analyzers that may include an already full schedule, thus increasing costs and reducing the availability of the laboratory analyzer. This solution may be expensive in terms of delays in reporting of the patient results, the additional quality control material consumed, the additional test reagents consumed, and the technologist's time and effort in the follow-up of any outlying data that are detected during the analysis of the additional quality control specimens.

Another solution to detect the intermittent errors may include using an adequately sensitive and specific patient data analysis technique to detect an error in a laboratory analyzer. One such technique includes monitoring interpatient medians or averages and deviations therefrom. Such techniques may provide details regarding a distribution of patient data and characteristics of the distribution. Various data reduction schemes have been used to provide averages or medians of truncated (e.g., trimmed) patient results. Unfortunately, while the deviation of patient results from the usual average or median can signal an analytic shift, it can also indicate a change in patient constituency, an analytic bias, or a combination thereof. Another disadvantage of such median or average tracking is that it detects an analytic shift or a systematic error, but does not detect an increase in random error.

About fifty years ago, Hoffman and Waid introduced the average of normal (AON) quality control (QC) method in their paper titled "The 'average of normals' method of quality control". Using AON, test results that are determined to be within a "normal" range of expected results (e.g., within a certain standard deviation of average) were averaged and that average was used to monitor changes in the laboratory equipment and/or process of analyzing specimens. Using AON either no error condition exists (patient average was within limits) or an error exists (patient average is outside of limits and presumably due to an analytical shift with the average of the results either increased or decreased). As laboratory results outside their usual limits tend to be repeated more often than normal results, Hoffman and Waid recommended that only results within the normal range be averaged.

In 1984, Cembrowski et al. assessed AON as an analysis tool in the publication titled "Assessment of 'average of normals' quality control procedures and guidelines for implementation." The simulations performed by Cembrowski showed that AON reliability depends on a number of factors such as number of samples divided by an analytical standard deviation (Sa) (i.e. the standard deviation inherent in the analysis procedure), a width of the range considered of samples considered "normal" samples, the number of "normal" samples used in determining the average after truncating samples outside of the normal range, and the range of the control limits for the average of the normal samples.

One of the most popular approaches to hematology QC is Bull's approach (also known as Xb, pronounced "x bar b") which uses a unique average of sequential batches of twenty patient red cell indices to demonstrate (in)stability in red cell associated Coulter measurements. The red cell indices consist of the directly measured mean corpuscular volume (MCV), the mean corpuscular hemoglobin calculated from hemoglobin (Hgb) and red blood cell (RBC) count, and the mean corpuscular hemoglobin concentration (MCHC) derived from Hgb, RBC and MCV. Too often, especially with today's highly precise hematology analyzers, these outlying average indices in hospital patients indicates the analysis of nonrandomized selection of patients with a high proportion of abnormal indices including neonates, renal failure patients or oncology patients undergoing chemotherapy.

In the 1980's and 1990's, review of control every twenty specimens may have had significant utility. Today, however, many more samples are being analyzed and QC review every twenty samples is cumbersome. To decrease the implicit variation of the patient average and to improve its error signaling, it may be intuitive to average more specimens. In an evaluation of patient averages, it was determined that the error-detection capabilities of patient averages depend on multiple factors with the most important being the number of patient results averaged (N) and the ratio of the standard deviation of the patient population (sp) to the standard deviation of the analytical method (sa). Other important factors included the limits for evaluating the mean (control limits), the limits for determining which patient data are averaged (truncation limits), and the magnitude of the population lying outside the truncation limits.

In one or more embodiments, it can be beneficial to prevent the averaging of specimens with outlying results. For example, in a referral laboratory which analyzes primarily specimens from generally healthy patients, the occasional incorporation of blood from a patient with renal failure or chemotherapy will not affect the patient mean if proper truncation limits are implemented.

To monitor laboratory analyzers, either middleware or the analyzer's own software can be programmed to refrain from averaging patients from specific units (renal failure, oncology) or patients of specific ages (i.e., the neonate). Before averaging, to reduce the effect of the more frequent testing of outlying abnormal results, these data can be excluded (truncated) from averaging.

In modern day applications of averages of patient data, intermittent transient shifts in the patient averages can largely be ignored. The trouble-shooting of persistently shifted patient averages can incorporate assessment of pre-analytical as well as post analytical (e.g., laboratory information) issues. The laboratorian should have an understanding of the clinical reasons for shifts in the patient averages before assuming analytical error and adjusting analyzer parameters. It is not always clear to laboratory staff whether a persistent shift is due to a subtle patient population shift or an altered analytical process. As such, the investigation of persistent outlying patient averages can be problematic. Techniques that employ patient averaging techniques may not easily detect random error.

Stability in the laboratory results of hospital patients can be seen in patients that are sampled (and analyzed) only once per day, such as between 0400 and 1200 hours in many hospitals. This stability arises from at least two different independent mechanisms: 1) for many laboratory tests, there is an implicit diurnal variation, so sampling and analyzing them on a 24 hour basis will tend to cause the least variation in their sequential results; and 2) in hospitals, patient acuity of illness is associated with more frequent testing. Thus, generally, only more stable patients will be sampled about once per 24 hours. The testing can occur in the morning because of requirements for tests in the fasting status and clinicians usually perform their testing rounds in the morning and require "fresh" laboratory results to help them determine the medical course of the patient.

The between day differences in the patient results is generally minimal. As such, the average difference of a specific laboratory result in all the patients who have their blood sampled only in the morning hours may be close to zero unless there is a persistent error in the analyzer or there is a trend in the patient data independent of the analyzer (this may be significant in only a few analytes).

Many laboratory tests are repeated (e.g., hourly, every day, or other time frame between tests). Patients who have repeat testing at most every day (e.g., somewhere between sixteen and thirty-two hours between analyte collection) are probably quite stable and are not being aggressively treated. These patients and their corresponding measurements can provide a basis for analyzing whether an operating laboratory analyzer needs recalibration or needs to be further investigated, repaired, and/or recalibrated.

Based on the high prevalence of about 24 hour repeats (about 70% of tests area repeated within forty-eight hours) and lower biologic variation at about 24 hours, patients retested at about 24 hours can be their own controls. A delta can be calculated (patient 1 (0 hours)–patient 1 (16 to 32 hours later)) for each data pair. The Standard Deviation of Duplicates (SDD) and/or average of deltas (AoD) can be calculated to determine systematic error in a laboratory analyzer and/or increased random error in the laboratory analyzer.

An AoD (e.g., a moving AoD) can be calculated, such as can include differences in an analyte measurement of a patient that is repeated within 16 and 32 hours. The AoD calculation is summarized as in Equation 1:

$$AoD = \sum_{i=1}^{N} \Delta_i / N. \qquad \text{Equation 1}$$

In Equation 1, $\Delta_i$ is the difference between consecutive analyte measurements of the same patient that is repeated within 16 to 32 hours and N is the number of deltas used in determining the average. If the AoD value is outside a range of acceptable AoD values, such as a standard deviation of AoD values being outside an acceptable range of standard deviation values, then an error condition can be signaled.

The deltas can be averaged, such as by using moving averages (i.e. AoDs), with an AoD or a standard deviation of AoDs exceeding a threshold indicating a significant analytical shift. A significant analytical shift can mean that the laboratory analyzer requires servicing, such as usually includes re-calibration. As analytical shifts can either represent a bad shift (going from a correct to an incorrect calibration state) or a good shift (going from an incorrect to a correct calibration state), a previous average, such as a prior day's average (mean, median, AoD, or mode), can be compared to the calculated average to determine if the shift is a good shift or a bad shift. A "normal" previous average with a higher positive or negative AoD can signal a developing error. A high previous average and a lower current average of deltas can indicate a situation in which the error condition is being corrected.

The standard deviation of the AoD can be calculated as in Equation 2

$$\sqrt{(\sum_{j=1}^{M} (AoD_j - AoD_\mu)^2/M)} \quad \text{Equation 2}$$

In Equation 2, $AoD_j$ is a determined AoD value, such as by using Equation 1, $AoD_\mu$ is the average of the M $AoD_j$ values, and M is the number of $AoD_j$ values used in the standard deviation calculation.

A specified number of delta calculations (e.g., AoDs) can be used for each calculation, such as to help ensure statistical significance. The specified group size can vary between analytes. If the AoD calculation is out of range, such as can be indicated by the SDD exceeding a specified SDD limit, then an error flag can be turned on.

Using software modeling of patient data collected during 669 days and selecting only those samples from patients that were repeated within 16-32 hours of the previous analysis the ability of the calculation to detect a simulated significant shift in instrument performance was demonstrated.

Each analyte to be considered for monitoring by the average of deltas (AoD) can have a unique requirement for the number of pairs (deltas) of samples to be averaged (N). Similarly, each analyte can have unique limits to the magnitude of deltas or individual analyte measurements that can be included in the calculation. In order to determine a set (e.g., an optimal set) of parameters for the AoD calculation for each analyte, the patient data pairs were analyzed via a computer script that induces a user defined error at increasing intervals throughout the data stream and calculates the average number of deltas to detection (ANDD), the standard deviation of the ANDD, mode number of deltas to detection (Mode NDD) and median number of deltas to detection (Median NDD). The computer script, using a simulated annealing algorithm stochastically selects the number of patient pairs to average (N) and the allowable magnitude of the delta pairs, or truncation limits, to use to minimize the ANDD value.

The truncation limits in effect exclude delta values greater than or less than a set limit from the ANDD calculation. Selection of the upper truncation limits (TLU) or lower (TLL) is intended to reduce the magnitude of the ANDD oscillations caused by large deltas. The exclusion of the larger deltas can serve at least two purposes. The first is that the AoD calculation relies on pairs of values from stable patients to determine the analytic performance of the instrument; pairs of samples with large deltas likely do not represent stable patients. The second purpose is strictly mathematical, large values when included in an average calculation will unduly pull the mean towards an extreme value. In general, the size of the allowable delta (e.g., an allowable measurement value) is a function of the difference between the concentrations of the analyte of interest between healthy and acutely ill patients, the maximal physiologically delta possible within 16-32 hours, and the magnitude of the analytical error or bias one is trying to detect.

As an example of this effect, simulations determined truncation limits for pairs of potassium results to be 1.20 and −1.59 mmol/L in order to detect a shift of +/−0.5 mmol/L. In contrast, for Alanine Aminotransferase, simulations determined truncation limits were determined to be 31 and −16 U/L to detect a shift of +/−7 U/L.

Using this system, the N value and truncation limits for each analyte to be monitored could be determined from a stream of historical data pairs. If the AoD shifts due to an out of control instrument condition, the AoD will exceed the user defined limit and the system or device will laboratory personnel to the error condition.

Reference will now be made to the FIGS. to describe further details of one or more embodiments.

FIG. 1 illustrates, by way of example, a block diagram of an embodiment of a system 100 to determine if a laboratory analyzer requires just re-calibration or a more complete investigation, which usually includes re-calibration. The system 100 as illustrated includes a laboratory analyzer 102 and an AoD module 104. The laboratory analyzer 102 can include a hematology, chemistry, or other analyte analyzer. The laboratory analyzer 102 can take an analyte 106 as an input and produce a result 108 that is a measurement of a property (e.g., height, width, volume, area, concentration, pH, or the like) of the analyte 106. The result 108 can be provided to the AoD module 104. The result 108 can include a tag that indicates the patient identity that the result 108 is associated with. The result can include a tag that indicates a time the analyte 106 was obtained from the patient. The tag information can be gathered manually, such as by a nurse, and input to the system 100, such as through a User Interface (UI) not shown in FIG. 1, or automatically entered, such as by a "smart" laboratory analyzer.

The AoD module 104 can determine an AoD of the results 108. The AoD module 104 can include a filter 110. The filter 110 can implement a value delta filter and/or a time delta filter that filters based on consecutive analyte results from the same patient. The filter 110 can compare the value deltas to a specified value delta threshold. The value delta threshold can be set by an expert or other personnel and can be set based on the analyte and the amount of error that is considered acceptable in the result without giving a false positive on determining that the laboratory analyzer 102 is to be calibrated. If a calculated value delta is greater than the value delta threshold, the filter 110 can remove the value delta from the results used by the AoD module 104 to calculate the AoD. Note that results can alternatively be filtered individually, such as to remove results above and/or below one or more specified limits. This can help ensure that the delta value calculations are within specification without needing to calculate the delta value.

Similarly, the filter 110 can compare the time delta to a specified time delta range. The specified time delta range can indicate a time range between deltas that is acceptable. For example, the time delta range can be between about sixteen and about thirty-two hours, about twenty and about twenty-eight hours, about twenty-two and about twenty-six hours, about twenty-three and a half hours and about twenty-four and a half hours, or the like. The closer the time delta range is to twenty-four hours, the lower a biologic variation is expected to be, thus a smaller value delta is expected. If the time delta between consecutive results for the same patient is outside of the time delta range, the filter 110 can remove the value(s) or the delta corresponding to the value(s) from the results to be used by the AoD module 104 to calculate the AoD.

The AoD module 104 can receive value deltas from the filter 110 that are less than the value delta threshold and whose time tags indicate that the time delta is within the time delta range. The AoD module 104 can determine an average (e.g., a moving average) of the value deltas from the filter 110. The AoD 112 can be provided to a compare module 114. The number of AoD values used to determine an AoD value can be predetermined, such as to help guarantee statistical significance.

The compare module 114 compares the AoD 112 to one or more AoD thresholds 116. The AoD threshold 116 defines acceptable AoD values. If the compare module 114 determines that the AoD 112 is not within the range of acceptable values, an indicator signal can be provided to an alert module 118. Additionally or alternatively, the compare module 114 can compare the AoD 112 to other AoDs, such as one or more of the most recent AoDs (a prior AoD, such as one or more immediately previous AoDs), to determine if there is a trend in the AoDs received. For example, the compare module 114 can determine that the most recent AoDs indicate that the AoDs are trending (increasing or decreasing) and that the laboratory analyzer 102 is to be calibrated or otherwise examined by the proper personnel. The compare module 114 can provide an indicator to the alert module 118 that causes the alert module 118 to transmit a message to the proper personnel.

The alert module 118 can provide a message to proper personnel indicating that the laboratory analyzer 102 is to be calibrated, such as by a lab technician, a laboratory analyzer manufacturer, personnel that can calibrate the laboratory analyzer 102, or other personnel. The message can include a text message, a phone call, such as an automated phone call with one or more standard messages, an email, a communication using a software chat program, an audible alarm, or other message. If recalibration is not successful in bringing the operation of the laboratory analyzer within tolerance levels then the operation of the laboratory analyzer should be investigated more thoroughly.

Figure 2:
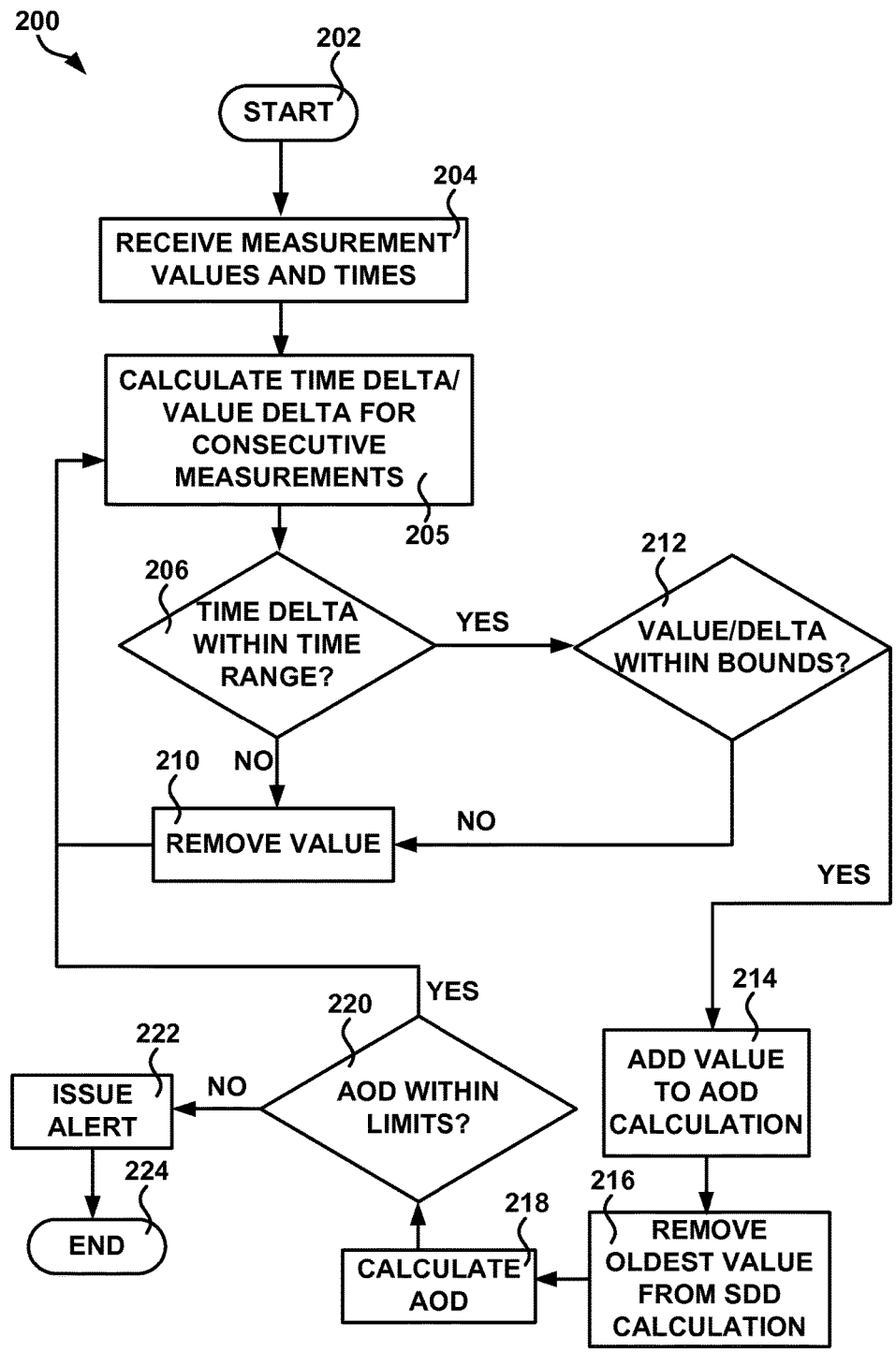
FIG. 2 illustrates, by way of example, a flow diagram of an embodiment of a method 200 of determining if a laboratory analyzer is to be calibrated.

FIG. 2 illustrates, by way of example, a flow diagram of an embodiment of a method 200 of determining if a laboratory analyzer is to be calibrated. The method 200 can be implemented using the system 100, for example. The method 200 as illustrated includes beginning at operation 202. At operation 204 measurement values and corresponding times can be received. The measurement values can include a time tag and/or a patient tag associated therewith. A time delta can be calculated for consecutive measurements of the same patient at operation 205.

At operation 206, it can be determined whether the time delta is within a specified time delta range. If the time delta is not within the time delta range then the measurement value can be removed at operation 210 and another time delta can be determined at operation 205. If the time delta is within the time delta range it can be determined if the measurement value (e.g., an individual value or a delta value) is within one or more specified measurement bounds at operation 212. If the value is not within the specified bounds, the measurement value can be removed at operation 210 and another time delta can be determined at operation 205. If the value delta is less than the value delta threshold, the value delta can be added to an AoD calculation at operation 214. At optional operation 216 a current oldest value (e.g., delta value) being used to calculate the AoD can be removed. Such a configuration provides a first in first out (FIFO) sort of calculation for the AoD. An alternative to the FIFO style calculation include waiting until a specified number of new values are received to calculate the AoD and waiting a specified amount of time before calculating the AoD, among other alternatives.

At operation 218 the AoD can be calculated using the determined and approved value. At operation 220 it can be determined whether the AoD is within specified limits. If the AoD is within the specified limits, the method 200 can resume at operation 205. If the AoD is not within the limits, an alert can be issued at operation 222. An alternative to determining if the AoD is less than the threshold at operation 220 includes determining if the AoD is trending either upward or downward so as to warrant issuing an alert at operation 222. In one or more embodiments, an alert may be sent only if consecutive AoD measurements (e.g., two, three, four, five, six, etc.) are outside the limits and/or if consecutive AoD measurements are trending in the same direction. The method 200 can end at operation 224.

FIG. 3 illustrates, by way of example, a table 300 of analyte (potassium in the example of FIG. 3) measurement values for a variety of patients and over a variety of time ranges. The table 300 as illustrated includes a variety of patients A, B, C, D, E, F, and G and four analyte measurements at a variety of time intervals for each patient. FIG. 4 illustrates, by way of example, a table 400 of time deltas and value deltas corresponding to the times a values of the table 300 of FIG. 3.

For explanation purposes, assume that a time delta range is set to be between and including twenty (20) and twenty-eight (28) hours and that a maximum measurement value is set to be five (5.0) and a minimum measurement value is set to be three (3.0). The time delta range and the maximum and minimum measurement value bounds define the delta values that will be used in an AoD calculation. In the example of the delta values of FIG. 4, value delta one and value delta two for patient D, value delta 2 for patient E, value delta 1 for patient F, and all value deltas for patient G would be filtered out of the set of value deltas used in the AoD calculation. This is because the time delta does not fall in the acceptable time delta range of between twenty and twenty-eight hours. None of the measurement values are filtered out because none of the measurement values are greater than five or less than three. Note that instead of defining upper and lower bounds on individual measurement values, a maximum delta value can be defined to filter out delta measurements. For example, the maximum delta in the example of FIGS. 3 and 4 can be set to two (2.0), the difference between the maximum and minimum measurement bounds. While a maximum delta can permit a value outside of the maximum and minimum value bounds to be used in an AoD calculation, it can still help ensure that the data is from stable patients and that it does not unduly skew the AoD calculation.

The value deltas remaining can be used in the AoD calculation. The result obtained using the AoD equation can be compared to a threshold value. The result obtained can be compared to one or more previous results (e.g., one or more of the most recent previous results). An alert can be transmitted to proper personnel if the result is greater than the threshold. The alert can indicate how much over the threshold the AoD value is and/or if the AoD is greater or less than a previous AoD value.

The time delta range and the maximum and minimum values are merely examples and the time delta range and the maximum and minimum values can be different values, such as for the same or different analyte. The time delta range can be chosen so as to reduce the incorporation of patients with increased biologic variation or to keep the biologic variation relatively stable. The value delta range can be set so as to reduce the influence of outlying values on the AoD calculation, such as to help increase the accuracy of the AoD calculation.

Figure 5:
FIG. 5 illustrates, by way of example, a table illustrating induced error, ANDD, SD, mode NDD, and median NDD for a plurality of analytes.

FIG. 5 illustrates, by way of example, a table 500 illustrating induced error, ANDD, SD, mode NDD, and median NDD for a plurality of analytes. The values of the table 500 were obtained using actual patient data and software modeling as previously discussed. The values ANDD, SD, mode NDD, and/or median NDD can be used to determine a truncation limit for an individual analyte value and/or a delta value and/or a range of acceptable AoD values.

Figure 6:
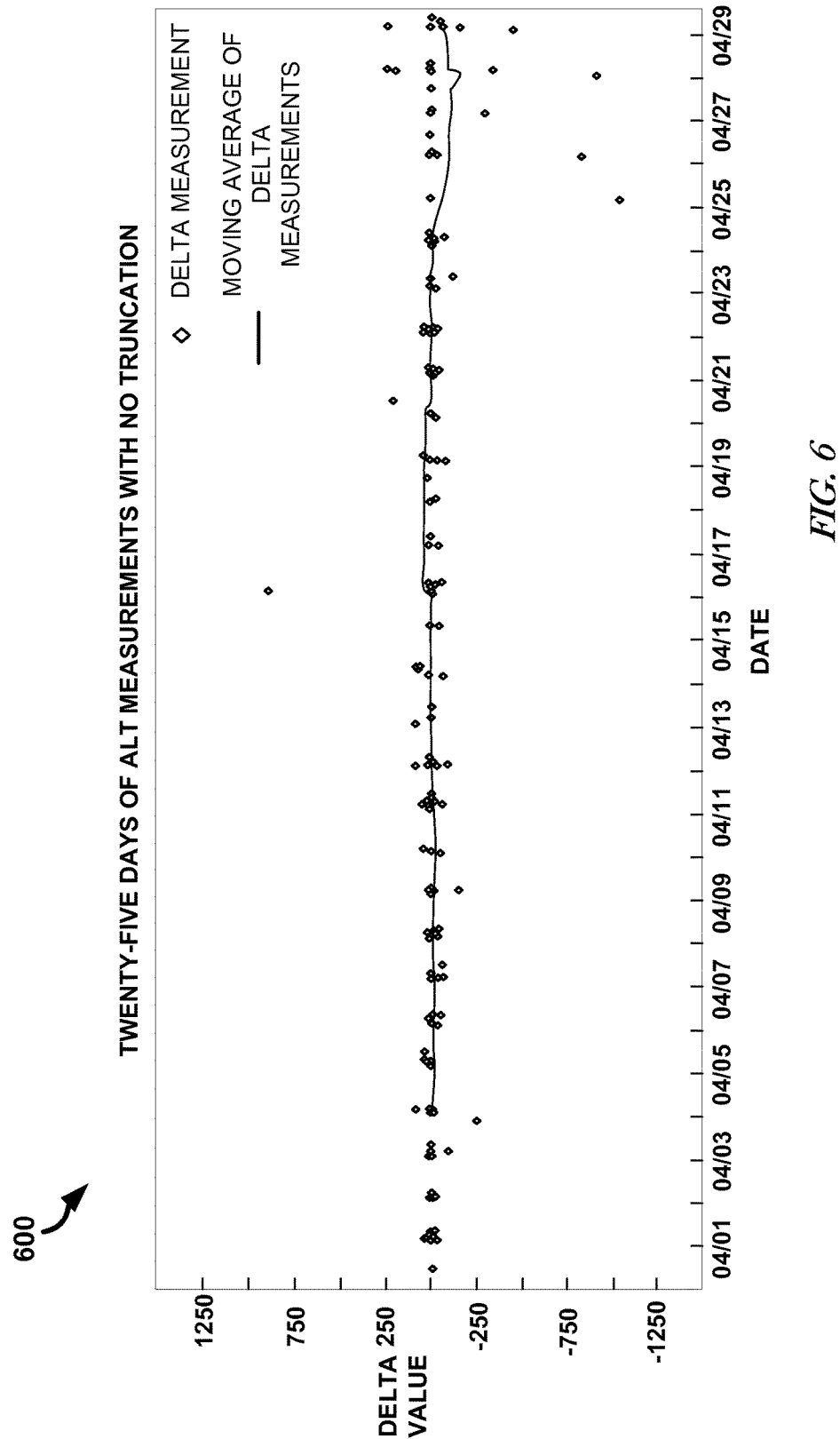
FIG. 6 illustrates, by way of example, a graph of delta values vs. time for twenty-five days of measurements of an ALT analyte performed using a laboratory analyzer.
Figure 7:
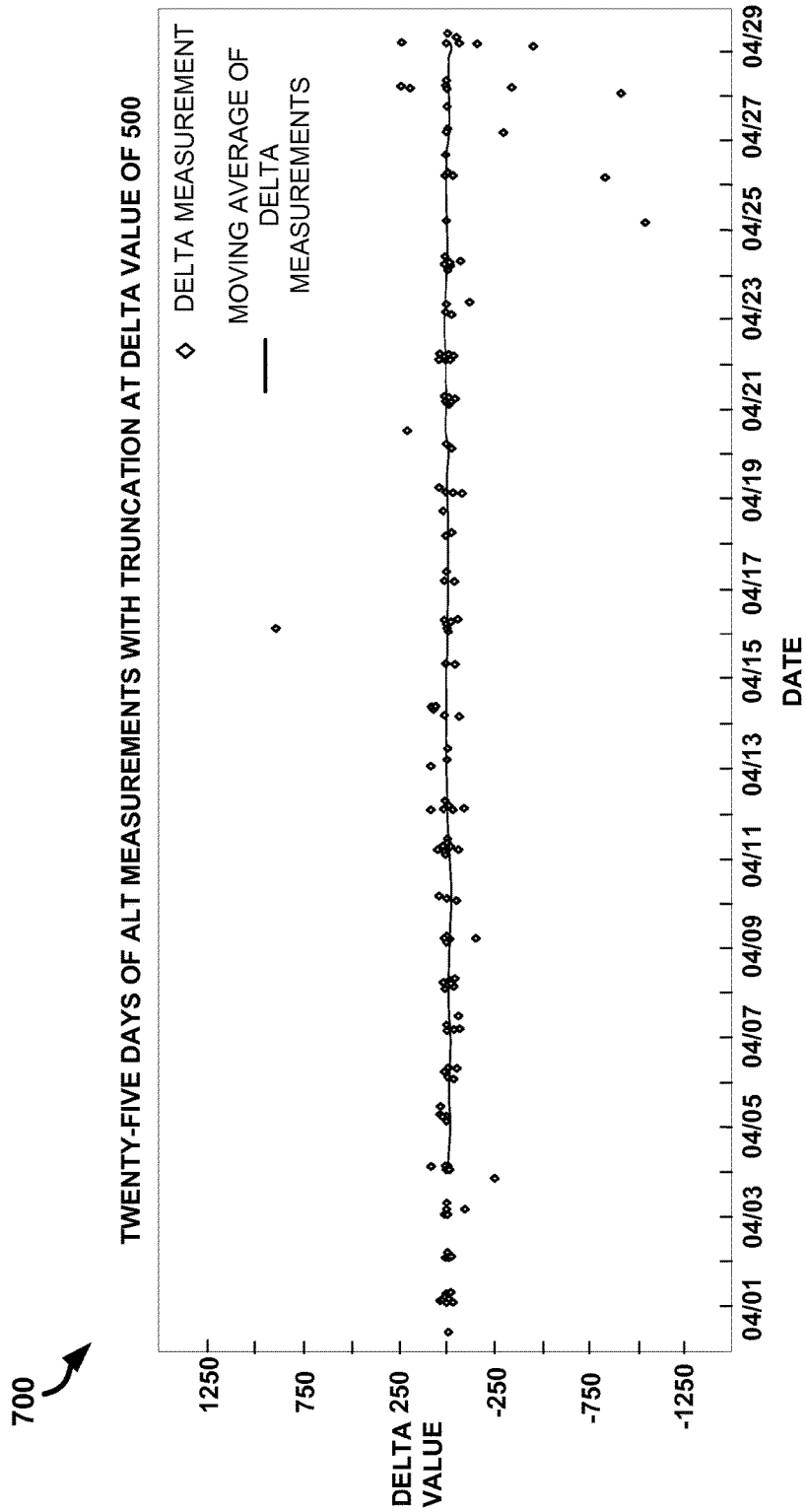
FIG. 7 illustrates, by way of example, a graph of delta values vs. time similar to the graph of FIG. 6, with the graph including truncation limits for a delta value with an absolute value of 500 or greater.

FIG. 6 illustrates, by way of example, a graph 600 of delta values vs. time for twenty-five days of measurements of an ALT analyte performed using a laboratory analyzer. As can be seen, the AoD can be significantly impacted from an analyte measurement that strays too far from the average. FIG. 7 illustrates, by way of example, a graph 700 of delta values vs. time similar to the graph 600, with the graph 700 including truncation limits for a delta value with an absolute value of 500 or greater. As can be seen in the graph 700, the AoD is more stable (less variation) with such a truncation.

Figure 8:
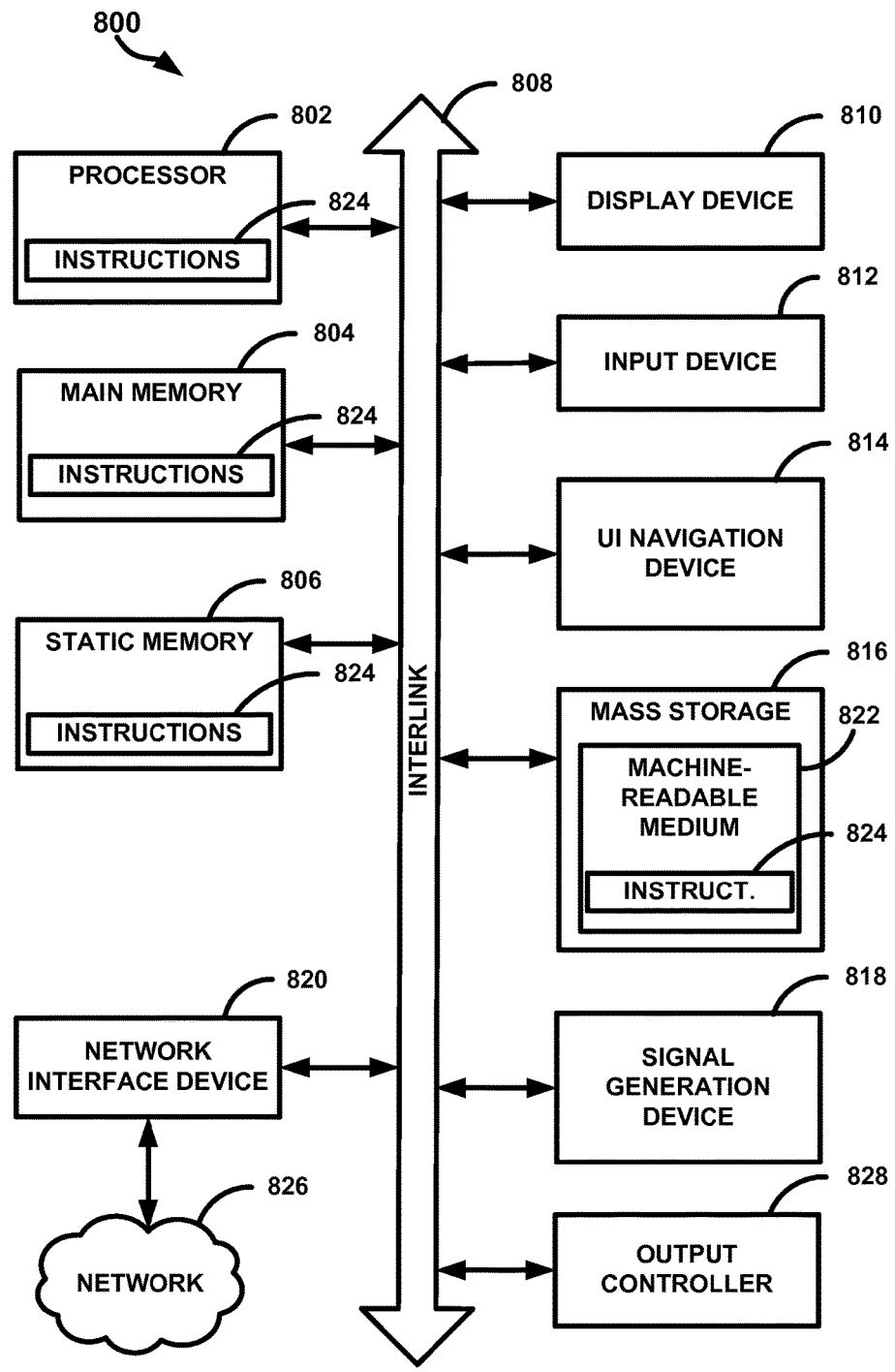
FIG. 8 illustrates, by way of example, a block diagram of an example of a device upon which any of one or more processes (e.g., methods) discussed herein can be performed.

FIG. 8 illustrates, by way of example, a block diagram of an example of a device 800 upon which any of one or more processes (e.g., methods) discussed herein can be performed. The device 800 (e.g., a machine) can operate so as to perform one or more of the programming or communication processes (e.g., methodologies) discussed herein. In some examples, the device 800 can operate as a standalone device or can be connected (e.g., networked) to one or more items of the system 100, such as the laboratory analyzer 102, the AoD module 104, the filter module 110, the compare module 114, and/or the alert module 118. An item of the system 100 can include one or more of the items of the device 800. For example one or more of the laboratory analyzer 102, the AoD module 104, the filter module 110, the compare module 114, and/or the alert module 118 can include one or more of the items of the device 800.

Embodiments, as described herein, can include, or can operate on, logic or a number of components, modules, or mechanisms. Modules are tangible entities (e.g., hardware) capable of performing specified operations when operating. A module includes hardware. In an example, the hardware can be specifically configured to carry out a specific operation (e.g., hardwired). In an example, the hardware can include configurable execution units (e.g., transistors, logic gates (e.g., combinational and/or state logic), circuits, etc.) and a computer readable medium containing instructions, where the instructions configure the execution units to carry out a specific operation when in operation. The configuring can occur under the direction of the executions units or a loading mechanism. Accordingly, the execution units can be communicatively coupled to the computer readable medium when the device is operating. In this example, the execution units can be a user of more than one module. For example, under operation, the execution units can be configured by a first set of instructions to implement a first module at one point in time and reconfigured by a second set of instructions to implement a second module.

Device (e.g., computer system) 800 can include a hardware processor 802 (e.g., a central processing unit (CPU), a graphics processing unit (GPU), a hardware processor core, processing circuitry (e.g., logic gates, multiplexer, state machine, a gate array, such as a programmable gate array, arithmetic logic unit (ALU), or the like), or any combination thereof), a main memory 804 and a static memory 806, some or all of which can communicate with each other via an interlink (e.g., bus) 808. The device 800 can further include a display unit 810, an input device 812 (e.g., an alphanumeric keyboard), and a user interface (UI) navigation device 814 (e.g., a mouse). In an example, the display unit 810, input device 812 and UI navigation device 814 can be a touch screen display. The device 800 can additionally include a storage device (e.g., drive unit) 816, a signal generation device 818 (e.g., a speaker), and a network interface device 820. The device 800 can include an output controller 828, such as a serial (e.g., universal serial bus (USB), parallel, or other wired or wireless (e g, infrared (IR), near field communication (NFC), etc.) connection to communicate or control one or more peripheral devices (e.g., a printer, card reader, etc.).

The storage device 816 can include a machine readable medium 822 on which is stored one or more sets of data structures or instructions 824 (e.g., software) embodying or utilized by any one or more of the techniques or functions described herein. The instructions 824 can also reside, completely or at least partially, within the main memory 804, within static memory 806, or within the hardware processor 802 during execution thereof by the device 800. In an example, one or any combination of the hardware processor 802, the main memory 804, the static memory 806, or the storage device 816 can constitute machine readable media.

While the machine readable medium 822 is illustrated as a single medium, the term "machine readable medium" can include a single medium or multiple media (e.g., a centralized or distributed database, and/or associated caches and servers) configured to store the one or more instructions 824. The term "machine readable medium" can include any tangible medium that is capable of storing, encoding, or carrying instructions for execution by the device 800 and that cause the device 800 to perform any one or more of the techniques (e.g., processes) of the present disclosure, or that is capable of storing, encoding or carrying data structures used by or associated with such instructions. The term "machine-readable medium" shall accordingly be taken to include, but not be limited to, solid-state memories, and optical and magnetic media. Specific examples of machine-readable media can include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks. A machine readable medium does not include signals per se.

The instructions 824 can further be transmitted or received over a communications network 826 using a transmission medium via the network interface device 820 utilizing any one of a number of transfer protocols (e.g., frame relay, internet protocol (IP), transmission control protocol (TCP), user datagram protocol (UDP), hypertext transfer protocol (HTTP), etc.). Example communication networks can include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 820 can include one or more physical jacks (e.g., Ethernet, coaxial, or phone jacks) or one or more antennas to connect to the communications network 826. In an example, the network interface device 820 can include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the device 800, and includes digital or analog communications signals or other intangible medium to facilitate communication of such software.

Examples and Notes

The present subject matter may be described by way of several examples.

Example 1 may include or use subject matter (such as an apparatus, a method, a means for performing acts, or a device readable memory including instructions that, when performed by the device, may cause the device to perform acts), such as may include or use determining a time delta between consecutive measurements of an analyte made on a patient using a laboratory analyzer, determining whether the time delta is within a specified time window, determining a measurement value delta between the first and second measurements if the time delta is within the specified window, calculating an average of deltas, the average of deltas including a measurement value delta between the consecutive measurements, determining whether the average of deltas is within a specified range of acceptable average of delta values, and/or issuing an alert if the average of deltas is not within the specified range of acceptable average of delta values.

Example 2 may include or use, or may optionally be combined with the subject matter of Example 1 to include or use, wherein the specified time window is between about sixteen and thirty-two hours.

Example 3 may include or use, or may optionally be combined with the subject matter of at least one of Examples 1-2 to include or use, wherein the specified time window is between about eighteen and thirty hours.

Example 4 may include or use, or may optionally be combined with the subject matter of at least one of Examples 1-3 to include or use, wherein the specified time window is between about twenty and twenty-eight hours.

Example 5 may include or use, or may optionally be combined with the subject matter of at least one of Examples 1-4 to include or use, wherein the specified time window is between about twenty-two and twenty-six hours.

Example 6 may include or use, or may optionally be combined with the subject matter of at least one of Examples 1-5 to include or use, wherein the consecutive measurements include a first measurement and a second measurement and the method further comprises comparing the second measurement to a range of acceptable measurement values and discarding the second measurement if the second sample is not within the range of acceptable measurement values.

Example 7 may include or use, or may optionally be combined with the subject matter of at least one of Examples 1-6 to include or use, wherein determining whether the average of deltas is within a specified range of acceptable average of delta values includes comparing a standard deviation of a plurality of consecutive average of delta values to a threshold standard deviation value and the method further comprises determining the laboratory analyzer is to be calibrated in response to determining the standard deviation is greater than the threshold standard deviation.

Example 8 may include or use subject matter (such as an apparatus, a method, a means for performing acts, or a device readable memory including instructions that, when performed by the device, may cause the device to perform acts), such as may include or use a processor, an average of deltas (AoD) module, stored on a memory and executable by the processor, that receives pairs of consecutive measurement values of an analyte of one or more patients, each pair of consecutive measurement values including a first measurement of an analyte obtained from a patient of the one or more patient at a first time and a second measurement of an analyte obtained from the patient at a second time after the first time, determines a time delta between each pair of consecutive measurement values, determines whether the time delta is within a specified time window, determines a measurement value deltas between each pair of consecutive measurement values that includes a time delta with the specified time window, and determines an AoD using the determined measurement value deltas, and a compare module, executable by the processor, to compare the determined AoD to a range of acceptable AoDs and whether a laboratory analyzer that performed the duplicate measurements needs to be re-calibrated based on the comparison.

Example 9 may include or use, or may optionally be combined with the subject matter of Example 8 to include or use, wherein the specified time window is between about sixteen and thirty-two hours.

Example 10 may include or use, or may optionally be combined with the subject matter of at least one of Examples 8-9 to include or use, wherein the specified time window is between about eighteen and thirty hours.

Example 11 may include or use, or may optionally be combined with the subject matter of at least one of Examples 8-10 to include or use, wherein the specified time window is between about twenty and twenty-eight hours.

Example 12 may include or use, or may optionally be combined with the subject matter of at least one of Examples 8-11 to include or use, wherein the specified time window is between about twenty-two and twenty-six hours.

Example 13 may include or use, or may optionally be combined with the subject matter of at least one of Examples 8-12 to include or use, wherein the AoD module further compares the measurement value deltas to a range of acceptable measurement value deltas and discards the measurement value delta if the measurement value delta is not within the range of acceptable measurement value deltas.

Example 14 may include or use, or may optionally be combined with the subject matter of at least one of Examples 8-9 to include or use an alert module that issues an indication that the AoD is greater than the threshold in response to the comparison module determining the AoD is greater than the threshold.

Example 15 may include or use subject matter (such as an apparatus, a method, a means for performing acts, or a machine readable storage device including instructions that, when performed by the machine, cause the machine to perform operations), such as may include or use determining a time delta between consecutive measurements of an analyte made on a patient using a laboratory analyzer, determining whether the time delta is within a specified time window, determining a measurement value delta between the first and second measurements if the time delta is within the specified window, calculating an average of deltas, the average of deltas including a measurement value delta between the consecutive measurements, determining whether the average of deltas is within a specified range of acceptable average of delta values, and/or issuing an alert if the average of deltas is not within the specified range of acceptable average of delta values.

Example 16 may include or use, or may optionally be combined with the subject matter of Example 15 to include or use, wherein the specified time window is between about sixteen and thirty-two hours.

Example 17 may include or use, or may optionally be combined with the subject matter of at least one of Examples 15-16 to include or use, wherein the specified time window is between about eighteen and thirty hours.

Example 18 may include or use, or may optionally be combined with the subject matter of at least one of Examples 15-17 to include or use, wherein the specified time window is between about twenty and twenty-eight hours.

Example 19 may include or use, or may optionally be combined with the subject matter of at least one of Examples 15-18 to include or use, wherein the specified time window is between about twenty-two and twenty-six hours.

Example 20 may include or use, or may optionally be combined with the subject matter of at least one of Examples 15-19 to include or use, wherein the instructions for determining whether the average of deltas is within a specified range of acceptable average of delta values includes instructions which, when executed by the machine, cause the machine to perform operations comprising comparing a standard deviation of a plurality of consecutive average of delta values to a threshold standard deviation value and determining the laboratory analyzer is to be calibrated in response to determining the standard deviation is greater than the threshold standard deviation.

The above detailed description includes references to the accompanying drawings, which form a part of the detailed description. The drawings show, by way of illustration, specific embodiments in which methods, apparatuses, and systems discussed herein may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

As used herein, a "-" (dash) used when referring to a reference number means "or", in the non-exclusive sense discussed in the previous paragraph, of all elements within the range indicated by the dash. For example, 103A-B means a nonexclusive "or" of the elements in the range {103A, 103B}, such that 103A-103B includes "103A but not 103B", "103B but not 103A", and "103A and 103B".

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments may be combined with each other in various combinations or permutations. The scope of the invention should be determined with reference to the appended claims, along with the full scope of equivalents to which such claims are entitled.

What is claimed is:

1. A method comprising:
   determining a time delta between consecutive measurements of an analyte made on a patient using a laboratory analyzer;
   determining whether the time delta is within a specified time window of sixteen and thirty-two hours;
   determining a measurement value delta between the first and second measurements only if the time delta is within the specified time window to reduce biologic variation in the measurements;
   calculating an average of deltas, the average of deltas including the determined measurement value delta between the consecutive measurements;
   determining whether the average of deltas is within a specified range of average of delta values; and
   calibrating the laboratory analyzer in response to determining the average of deltas is not within the specified range of average of delta values.

2. The method of claim 1, wherein the specified time window is between eighteen and thirty hours.

3. The method of claim 2, wherein the specified time window is between twenty and twenty-eight hours.

4. The method of claim 3, wherein the specified time window is between twenty-two and twenty-six hours.

5. The method of claim 1, wherein the consecutive measurements include the first measurement and the second measurement and the method further comprises comparing the second measurement to a range of measurement values and discarding the second measurement if the second sample is not within the range of measurement values.

6. The method of claim 1, wherein determining whether the average of deltas is within a specified range of average of delta values includes comparing a standard deviation of a plurality of consecutive average of delta values to a threshold standard deviation value and the method further comprises determining the laboratory analyzer is to be calibrated in response to determining the standard deviation is greater than the threshold standard deviation.

7. A system comprising:
   a processor;

a memory including instructions that, when executed by the processor, causes the processor to implement an average of deltas (AoD) module that:

receives pairs of consecutive measurement values of an analyte of one or more patients, each pair of consecutive measurement values including a first measurement of an analyte obtained from a patient of the one or more patients at a first time and a second measurement of an analyte obtained from the patient at a second time after the first time;

determines a time delta between each pair of consecutive measurement values;

determines whether the time delta is within a specified time window of between sixteen and thirty-two hours;

determines a measurement value delta between each pair of consecutive measurement values only if the determined time delta is within the specified time window to reduce biologic variation in the measurements; and determines an AoD using the determined measurement value delta; and a compare module, executable by the processor, that compares the determined AoD to a range of AoDs and issues an alert that causes a laboratory analyzer that performed the consecutive measurements to be calibrated in response to determining the AoD is not within the range of AoDs.

8. The system of claim 7, wherein the specified time window is between eighteen and thirty hours.

9. The system of claim 8, wherein the specified time window is between twenty and twenty-eight hours.

10. The system of claim 9, wherein the specified time window is between twenty-two and twenty-six hours.

11. The system of claim 7, wherein the AoD module further compares the measurement value delta to a range of measurement value deltas and discards the measurement value delta if the measurement value delta is not within the range of measurement value deltas.

12. The system of claim 7, further comprising instructions on the memory, that, when executed by the processor, cause the processor to implement an alert module that issues an indication that the AoD is greater than the threshold in response to the comparison module determining the AoD is greater than the threshold.

13. A non-transitory machine readable storage device comprising instructions stored thereon, which when executed by the machine, cause the machine to perform operations comprising:

determining a time delta between consecutive measurements of an analyte made on a patient using a laboratory analyzer;

determining whether the time delta is within a specified time window of between sixteen and thirty-two hours;

determining a measurement value delta between the first and second measurements only if the time delta is within the specified window to reduce biologic variation of the measurements;

calculating an average of deltas, the average of deltas including a measurement value delta between the consecutive measurements;

determining whether the average of deltas is within a specified range of average of delta values; and issuing an alert that causes the laboratory analyzer to be calibrated in response to determining that the average of deltas is not within the specified range of average of delta values.

14. The storage device of claim 13, wherein the specified time window is between eighteen and thirty hours.

15. The storage device of claim 14, wherein the specified time window is between twenty and twenty-eight hours.

16. The storage device of claim 15, wherein the specified time window is between twenty-two and twenty-six hours.

17. The storage device of claim 13, wherein the instructions for determining whether the average of deltas is within a specified range of average of delta values includes instructions which, when executed by the machine, cause the machine to perform operations comprising comparing a standard deviation of a plurality of consecutive average of delta values to a threshold standard deviation value and determining the laboratory analyzer is to be calibrated in response to determining the standard deviation is greater than the threshold standard deviation.

* * * * *